(12) United States Patent
Molander

(10) Patent No.: US 8,496,640 B2
(45) Date of Patent: Jul. 30, 2013

(54) RELEASE TAPE-FREE FASTENERS AND DISPOSABLE ABSORBENT ARTICLES UTILIZING THE SAME

(75) Inventor: John Molander, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 265 days.

(21) Appl. No.: 12/754,232

(22) Filed: Apr. 5, 2010

(65) Prior Publication Data

US 2010/0191211 A1      Jul. 29, 2010

Related U.S. Application Data

(62) Division of application No. 11/585,379, filed on Oct. 24, 2006, now abandoned.

(51) Int. Cl.
*A61F 13/15*      (2006.01)
(52) U.S. Cl.
USPC ............................ 604/389; 604/390; 604/391
(58) Field of Classification Search
USPC ............................................ 604/389, 385.23
See application file for complete search history.

(56) References Cited

U.S. PATENT DOCUMENTS

| | | |
|---|---|---|
| RE26,151 E | 1/1967 | Duncan et al. |
| 3,692,618 A | 9/1972 | Dorschner et al. |
| 3,802,817 A | 4/1974 | Matsuki et al. |
| 3,848,594 A | 11/1974 | Buell |
| 3,860,003 A | 1/1975 | Buell |
| 4,081,301 A | 3/1978 | Buell |
| 4,322,875 A | 4/1982 | Brown et al. |
| 4,340,563 A | 7/1982 | Appel et al. |
| 4,430,148 A | 2/1984 | Schaefer |
| 4,573,986 A | 3/1986 | Minetola et al. |
| 4,610,678 A | 9/1986 | Weisman et al. |
| 4,673,402 A | 6/1987 | Weisman et al. |
| 4,695,278 A | 9/1987 | Lawson |
| 4,701,179 A | 10/1987 | Kellenberger et al. |
| 4,795,454 A | 1/1989 | Dragoo |
| 4,823,783 A | 4/1989 | Willhite, Jr. et al. |
| 4,846,815 A | 7/1989 | Scripps |
| 4,900,317 A | 2/1990 | Buell |
| 4,963,140 A | 10/1990 | Robertson et al. |
| 5,019,065 A | 5/1991 | Scripps |
| 5,032,122 A | 7/1991 | Noel et al. |
| 5,053,028 A | 10/1991 | Zoia et al. |

(Continued)

FOREIGN PATENT DOCUMENTS

| | | |
|---|---|---|
| GB | 1516287 | 7/1978 |
| JP | 11-276524 A | 10/1999 |

(Continued)

*Primary Examiner* — Susan Su
(74) *Attorney, Agent, or Firm* — Thibault Fayette; Charles R. Ware

(57) ABSTRACT

Disclosed herein are fasteners for disposable absorbent articles and disposable absorbent articles that include the fasteners. The disclosed fasteners generally are free of release tape and adhesives requiring those tapes. At the same time, the disclosed fasteners can be maintained in a closed position prior to the fastener's (and the disposable absorbent article's) use and during the process by which the article is manufactured. While maintainable in this closed position, the fastener may be easily opened by the consumer such that the fastener can be then used for its intended purpose, such as, for example to form a side closure on a diaper around the waist and legs of an infant.

16 Claims, 11 Drawing Sheets

U.S. PATENT DOCUMENTS

| | | | |
|---|---|---|---|
| 5,108,384 A * | 4/1992 | Goulait | 604/390 |
| 5,176,670 A | 1/1993 | Roessler et al. | |
| 5,176,671 A | 1/1993 | Roessler et al. | |
| 5,374,262 A | 12/1994 | Keuhn, Jr. et al. | |
| 5,537,722 A | 7/1996 | Niederhofer et al. | |
| 5,605,735 A | 2/1997 | Zehner et al. | |
| 5,611,789 A | 3/1997 | Seth | |
| 5,614,281 A | 3/1997 | Jackson et al. | |
| 5,674,216 A | 10/1997 | Buell et al. | |
| 5,897,546 A * | 4/1999 | Kido et al. | 604/391 |
| 5,926,926 A | 7/1999 | Kato | |
| 5,961,761 A * | 10/1999 | Heindel et al. | 156/163 |
| 5,969,025 A | 10/1999 | Corzani | |
| 6,030,373 A | 2/2000 | VanGompel et al. | |
| 6,428,526 B1 | 8/2002 | Heindel et al. | |
| 6,476,289 B1 | 11/2002 | Buell et al. | |
| 7,455,665 B2 | 11/2008 | Wendelstorf et al. | |
| 7,524,314 B2 | 4/2009 | Otsubo | |
| 7,569,040 B2 | 8/2009 | Nakahata et al. | |
| 7,608,068 B2 | 10/2009 | Fujioka | |
| 7,766,890 B2 | 8/2010 | Ito et al. | |
| 2004/0254558 A1 | 12/2004 | Minato, Jr. | |
| 2005/0197642 A1 | 9/2005 | Cheng | |

FOREIGN PATENT DOCUMENTS

| | | |
|---|---|---|
| JP | 2002-045214 A | 2/2002 |
| JP | 2003-235897 | 8/2003 |
| JP | 2003-299693 A | 10/2003 |
| JP | 2004-298455 A | 10/2004 |
| JP | 2006-175104 A | 7/2006 |
| WO | WO 97/28774 | 7/1997 |
| WO | WO 02/056814 | 7/2002 |

* cited by examiner

RELEASE TAPE-FREE FASTENERS AND DISPOSABLE ABSORBENT ARTICLES UTILIZING THE SAME

CROSS REFERENCE TO RELATED APPLICATION

This application is a divisional of prior U.S. application Ser. No. 11/585,379, filed on Oct. 24, 2006, now abandoned the substance of which is hereby incorporated by reference.

FIELD OF THE INVENTION

The present invention generally relates to fasteners for disposable absorbent articles and the articles themselves and, more specifically, to fasteners that are free of release tape and adhesives customarily associated with the release tape.

BACKGROUND OF THE INVENTION

Fasteners are useful to secure the corners of a disposable absorbent article, such as a diaper. Certain fasteners are refastenable in that they are capable of multiple openings and closures. These fasteners are useful, for example, to attach the absorbent article around the waist of a wearer and maintain the absorbent article on the wearer during use. In addition, these fasteners allow the diaper to be folded or rolled into a tight package for disposal, secured in a disposal configuration, and thereafter more easily disposed in a waste receptacle. When the fasteners are secured in the disposal configuration, the contents of the absorbent article are generally prevented from spilling or leaking out while the absorbent article is being disposed. Examples of these fasteners are generally described in Duncan et al. U.S. Pat. No. RE 26,151, Buell U.S. Pat. No. 3,848,594, Scripps U.S. Pat. No. 4,846, 815, Robertson et al. U.S. Pat. No. 4,963,140, Scripps U.S. Pat. No. 5,019,065, Noel et al. U.S. Pat. No. 5,032,122, Zoia et al. U.S. Pat. No. 5,053,028, Seth U.S. Pat. No. 5,611,789, and International Publication No. WO 02/056814 A1. These fasteners can include a mechanical fastener and/or an adhesive fastener.

Mechanical fasteners capable of refastenability include hook (or mushroom-shaped) fasteners engageable with loops, and variants thereof. These fasteners are generally rigid, but can be damaged during high-speed processes used to manufacture commercial quantities of consumer goods such as diapers. These processes are often referred to in the art as "conversion" processes. Damage occurs when the fasteners become inadvertently exposed to the processing equipment, which can destroy the fastener or diminish its usefulness by, for example, crushing elements of the fasteners. Hook fasteners are particularly vulnerable to such damage, but other mechanical type fasteners such as buttons, tab and slots, or the like can also become damaged, torn, or otherwise adversely affected by high speed processing.

Attempts to address these vulnerabilities have included designing fasteners and delicate elements thereon that are less likely to come into contact with the high-speed processing equipment. Generally, the designs include folding the fastener into a "closed" position and maintaining the fastener in that position throughout the manufacturing process and until the article is ready for use. Fasteners are generally maintained in the closed position by a pressure sensitive adhesive and a release surface, fused welds, or mechanical engagement of fastener elements directly into the article fabric adjacent the fastener.

Seth U.S. Pat. No. 5,611,789, for example, discloses a fastener design similar to designs that have been incorporated into commercially-available disposable absorbent articles. The '789 patent describes a fastener arrangement where mechanical fastening elements are disposed on a fastening tab formed of a backing and an adhesive layer. The adhesive layer also permanently attaches the fastening tab to a portion of the disposable absorbent article, which article includes a backsheet and a topsheet. A release tape is affixed to the topsheet by an adhesive and the release tape permits the user to release the fastening tab from the fastener arrangement prior to use, for example, and thereafter attach the fastening elements to a complementary fastening surface on the article when the article is ready for use, or attach the adhesive layer (exposable by the release tape) to other portions of the article after the article has been used and is ready to be disposed. While this fastener arrangement is suitable for maintaining the fastener in a closed position prior to use, it also requires materials such as a release tape and an adhesive layer (exposable by the release tape) to maintain the fastener in the closed position. These materials can complicate the conversion process and, or course, add to the costs of the article.

Heindel et al. U.S. Pat. No. 5,961,761 discloses another fastener design similar to designs that also have been incorporated into commercially-available disposable absorbent articles. This design does not require the adhesive layer and the release tape to maintain the fastener in the closed position prior to use. Specifically, mechanical fastening elements (i.e., hooks) on the fastener are releasably engageable with an inside surface of an ear tab on the article to maintain the fastener in the closed position prior to use. According to the '761 patent's disclosure, the ear tab to which the fastening elements releasably engage is formed of a material such as that used to form an outside cover or inside liner of the article, such as films, nonwoven materials, woven or knit materials, foams, composites, and laminates thereof.

Although the design disclosed in the '761 patent does not, according to the '761 patent's disclosure, require a release tape and or an adhesive layer exposable by the release tape, that design also does not ensure that the fastener will actually remain suitably engaged with the surface of the ear tab prior to its use and, therefore, does not ensure that the fastener (and the fastening elements thereon) will avoid damage from the conversion process. Specifically, the fastener in its closed position may encounter stresses during the conversion process stronger than the (peel) force and shear strength required to open the fastener. The fastener will undesirably open in response to those stresses, and, when opened during the conversion process, the fastening elements on the fastener will be vulnerable to damage by the conversion process equipment. If damaged, of course, the fastener will not work as intended to form a closure with other portions of the article.

One response to the problems associated with the fastener design disclosed in the '761 patent might be to incorporate loop fastening elements that complimentarily engage the hooks on the fastener. With this modification, a stronger (peel) force and shear strength are required to open the fastener. However, use of both of the hook and loop fastening elements to hold the fastener closed may provide a (peel) force and shear strength in excess of that ordinarily desired by the user (e.g., a parent) when attempting to place and fit the article around the waist of the wearer (e.g., an infant). For example, when the peel force is too great, the user will have difficulty in opening the fastener, while also handling and positioning the wearer. Consumer testing has shown that fastening systems exhibiting a peel force of greater than about 12 N/inch, as measured by a T-Peel Test, are viewed as being difficult to separate. Consumers tend to prefer a fastening system exhibiting a peel force of less than 10 N/inch, as measured by the T-Peel Test.

The foregoing discussion of conventional fastener designs identifies deficiencies in those designs such as, for example, the expense necessitated by the use of extra materials (e.g., release tape/surface and the adhesive exposed by the tape/surface), extra capital equipment (required to process a fastener having the extra materials), undesirably weak closure bonds that open during the diaper conversion process (resulting in damage to the fastener elements), and undesirably strong closure bonds that make use of the article by the consumer difficult and possibly impractical. Even if the expense necessitated by the extra materials were of no concern, the presence of such materials presents other potentially undesirable effects. For example, a pressure sensitive adhesive (and release tape) may undesirably adhere to the skin of the article's wearer (e.g., an infant) or to the hands of the article's user (e.g., a parent) when placing the article on the wearer. This problem might compel the article's user to select a different product that is less likely to offer this problem.

Accordingly, it would be desirable to provide a fastening system that eliminates the necessity of certain materials used in conventional fastening systems. Furthermore, it would also be desirable to provide a fastening system that maintains the structural integrity and conveniences that consumers have come to expect. Still further, it would be desirable to provide a fastening system that provides a temporary releasable bond maintaining the fastener in a closed position during processing and until ready for use. It would also be desirable to provide consumer goods, such as disposable absorbent articles, that incorporate such a fastening system.

SUMMARY OF THE INVENTION

Disclosed herein are fasteners for disposable absorbent articles and disposable absorbent articles that include the fasteners. The disclosed fasteners avoid one or more of the shortcomings present in the existing art. Specifically, the disclosed fasteners are free of release tape and the adhesives that required those tapes. At the same time, the disclosed fasteners can be maintained in a closed position prior to the fastener's (and the disposable absorbent article's) use, and during the process by which the article is manufactured. While maintainable in this closed position, the fastener may be easily opened by the consumer such that the fastener can be then used for its intended purpose, such as, for example to form a side closure on a diaper around the waist and legs of an infant. Various embodiments of the fastener and the disposable absorbent article containing the fastener are disclosed herein.

For example, a first embodiment of the fastener, free of a release tape, includes a fixed portion attachable to the article, a connective portion joined to and contiguous with the fixed portion, and a folding line disposed between the fixed and connective portions. The connective portion includes a distal edge. The connective portion also includes a fastening member having a fastening surface and a bonding surface opposite to the fastening surface, wherein the fastening surface is releasably fastenable to a layer of napped nonwoven fabric on the article. The connective portion also includes a backing member attached to the bonding surface of the fastening member. The presence of the layer of napped nonwoven fabric provides a surface to which the fastening surface of the fastener can temporarily bond and, together, can maintain the fastener in a closed position until the article is ready for use.

A second embodiment of the release tape-free fastener includes a fixed portion attachable to the article, a connective portion joined to and contiguous with the fixed portion, and a folding line disposed between the fixed and connective portions. The connective portion includes a distal edge. The connective portion also includes a fastening member having dissimilar proximate and distal fastening surfaces and a bonding surface opposite to the fastening surfaces, wherein at least one of the fastening surfaces is fastenable to a layer of shedable nonwoven fabric on the article. The connective portion also includes a backing member attached to the bonding surface of the fastening member. The presence of the layer of shedable nonwoven fabric provides a surface to which at least one of the fastening surfaces of the fastener can temporarily bond and, together, can maintain the fastener in a closed position until the article is ready for use.

A third embodiment of the release tape-free fastener includes a fixed portion attachable to the article, and a connective portion joined to and contiguous with the fixed portion. The connective portion includes a distal edge, and proximate and distal fastening members. Each of these fastening members includes a fastening surface and a bonding surface opposite to the fastening surface, wherein the fastening surfaces are releasably fastenable to each other. The connective portion also includes a backing member attached to the bonding surfaces of the proximate and distal fastening members. In addition to the fixed and connective portions, the fastener includes a folding line disposed between the proximate and distal fastening members. The presence of fastening surfaces that are releasably fastenable to each other enables the fastener to be maintained in a closed position until the article is ready for use.

As indicated above, also disclosed herein are disposable absorbent articles that include these fastener embodiments. The article generally includes a body portion having an inside surface, an outside surface opposite of the inside surface, longitudinal edges, end edges, a first end region, and a second end region opposite of the first end region. The body portion includes a liquid pervious topsheet, a liquid impervious backsheet joined to the topsheet, and an absorbent core disposed between the topsheet and the backsheet. The article also includes the first embodiment of the release tape-free fastener described above. Specifically, the fastener includes a fixed portion attached to the first end region of the body portion, a connective portion joined to and contiguous with the fixed portion, and a folding line disposed between the fixed and connective portions. The connective portion includes a distal edge. The connective portion also includes a fastening member having a fastening surface and a bonding surface opposite to the fastening surface, wherein the fastening surface is releasably fastenable to a layer of napped nonwoven fabric on the article. The connective portion also includes a backing member attached to the bonding surface of the fastening member. As indicated above, the presence of the layer of napped nonwoven fabric provides a surface to which the fastening surface of the fastener can temporarily bond and, together, can maintain the fastener in a closed position until the article is ready for use.

Alternatively, the article can include the second embodiment of the release tape-free fastener described above. Accordingly, the article has a fastener that includes a fixed portion attached to the first end region of the body portion, a connective portion joined to and contiguous with the fixed portion, and a folding line disposed between the fixed and connective portions. The connective portion includes a distal edge. The connective portion also includes a fastening member having dissimilar proximate and distal fastening surfaces and a bonding surface opposite to the fastening surfaces, wherein at least one of the fastening surfaces is fastenable to a layer of shedable nonwoven fabric on the inside surface of the body portion adjacent the fastener. The connective portion also includes a backing member attached to the bonding surface of the fastening member. As stated above, the presence of the layer of shedable nonwoven fabric provides a surface to which at least one of the fastening surfaces of the fastener can temporarily bond and, together, can maintain the fastener in a closed position until the article is ready for use.

In yet another alternative, the article can include the third embodiment of the release tape-free fastener described above. The article has a fastener that includes a fixed portion attached to the first end region of the body portion, and a connective portion joined to and contiguous with the fixed portion. The connective portion includes a distal edge. The connective portion also includes proximate and distal fastening members each having a fastening surface and a bonding surface opposite to the fastening surface, wherein the fastening surfaces are releasably fastenable to each other. The connective portion also includes a backing member attached to the bonding surfaces of the proximate and distal fastening members. In addition to the fixed and connective portions, the fastener includes a folding line disposed between the proximate and distal fastening members. As stated above, The presence of fastening surfaces that are releasably fastenable to each other enables the fastener to be maintained in a closed position until the article is ready for use.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
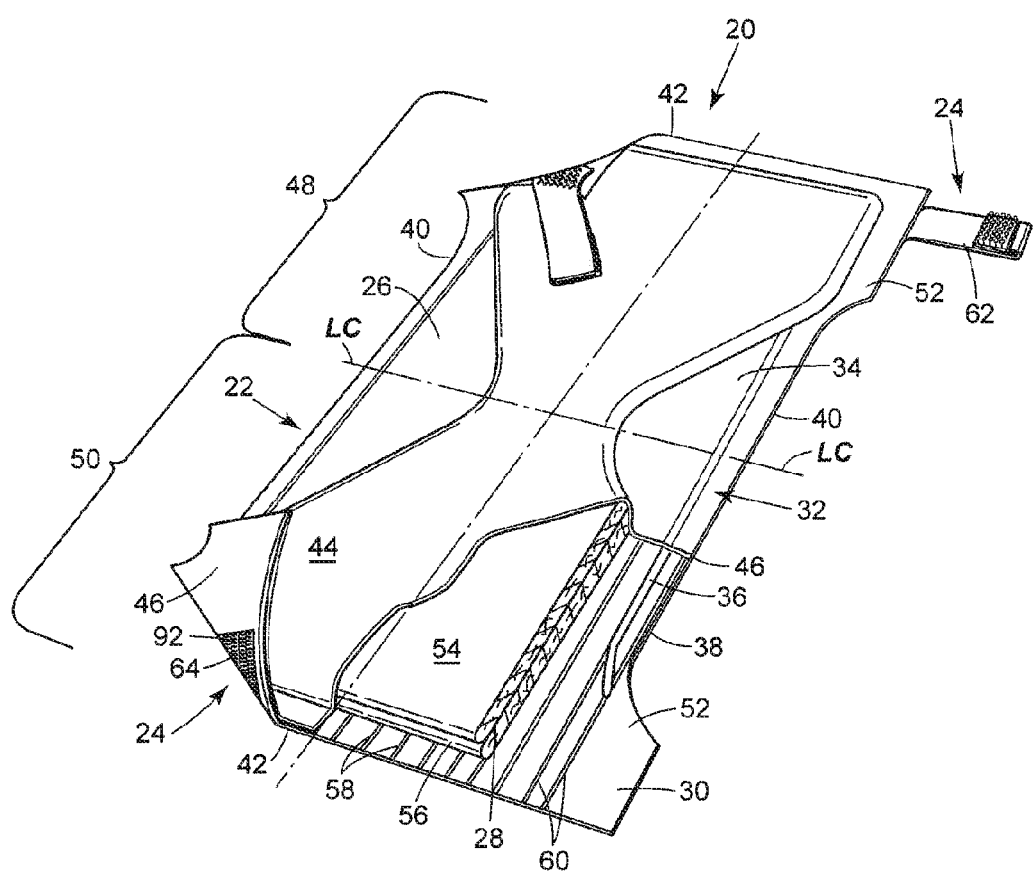
FIG. 1 is a partially cut-away perspective view of an embodiment of a disposable absorbent article specifically a diaper, incorporating a fastener embodiment of the present invention.

Disclosed herein are fasteners for disposable absorbent articles that address one or more of the above-described shortcomings associated with conventional fasteners. Also disclosed herein are disposable absorbent articles that include these fasteners.

"Absorbent article" is used herein to refer to a device that absorbs and contains liquid, and more specifically, refers to a device that is placed against or in proximity to a device wearer's body to absorb and contain various exudates discharged from the body. Absorbent articles include items such as diapers, pull-on diapers or pant-type garments, training pants, incontinence briefs, incontinence undergarments, absorbent inserts, diaper holders and liners, feminine hygiene garments, and the like.

"Disposable" is used herein to refer to describe absorbent articles that generally are not intended to be laundered or otherwise restored or reused as an absorbent article (i.e., articles intended to be discarded after a single use and, possibly, to be recycled, composted or otherwise disposed of in an environmentally compatible manner).

"Pant-type" is used herein to refer to an article configured such that it has a waist opening and a pair of leg openings. A pant may be placed in position on the wearer by inserting the wearer's legs into the leg openings and sliding the pant into position about a wearer's lower torso. This configuration may be permanent as in the case of conventional underwear, or may be temporary as in the case of a training pant with openable seams for removal. Additionally, absorbent articles can be constructed with refastenable features allowing the article to have both a pant-like configuration and one or more configurations which are open or not pant like.

"Longitudinal" is used herein to refer to a direction running perpendicular from a waist edge to an opposing waist edge of the article and generally parallel to the maximum linear dimension of the article. Directions within 45 degrees of the longitudinal direction are considered to be "longitudinal."

"Lateral" is used herein to refer to a direction running from a side edge to an opposing side edge of the article and generally at a right angle to the longitudinal direction. Directions within 45 degrees of the lateral direction are considered to be "lateral."

As used herein, the terms "elastic," "elastomer," "elastomeric," "elastically," and "stretchable" generally refer to materials which are extensible by a pulling force, and which also return to substantially their original dimensions when the external pulling force is removed. More specifically, these terms refer to a material that is able to extend to a strain of at least 50% without breaking or rupturing, and is able to recover substantially to its original dimensions after the deforming force has been removed. It will be appreciated that these terms include the term "extensible" as each term is used herein.

"Garment-facing" is used herein to refer to describe a surface that is in contact with or may be in close proximity to any garment being worn.

"Body-facing" is used herein to refer to describe a surface that is in contact with the body of a wearer or in close proximity (i.e., closer to the body than a garment-facing surface) to the body of the wearer when the article is worn.

"Disposed" is used herein to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "fixed," as used when referring to elements that are "fixed" to one another, means the elements are ordinarily joined or attached together by the manufacturer of the article in a manner such that the wearer or user of the article will not be able to un-join or detach the elements during the article's ordinary use, and the elements will not become un-joined or detached through the article's ordinary wear and tear. Elements that are "fixed" to one another are not intended to be separated during normal use of the article.

As used herein, the terms "refastenable," "releasably fastenable," and "engageable" refer to attachment of two or more elements or portions of elements together in a manner in which they can be separated and re-attached without substantial degradation of fastener performance or damage to surrounding components of the article which would impair the article's continued use. It will be appreciated that a refastenable, releasably fastenable, or engageable component need not have an infinite life span, but it is sufficient that the components attached in a refastenable, releasably fastenable, or engageable manner can be separated and re-attached successively several times over the typical use life span of the article. It will also be appreciated that the aggressiveness of actual fastening may be reduced significantly from fastening to refastening in absolute terms, but that such reduction is not "substantial degradation" of fastener performance if the resulting refastened strength is sufficient for purposes of ordinarily using the article and fastener.

"Mechanical fastener" is used herein to refer to a fastening system or mechanism relying on physical restraint, magnetic fields, or engagement of portions of the fastener for operation. Examples of mechanical fasteners are hook and loops, hooks and hooks, buttons, snaps, tab and slot, zippers, magnet(s), and tongue and groove fasteners.

Disclosed herein are improvements to fasteners used to secure and form side closures on disposable absorbent articles. These improvements include the elimination of and reduced expenses associated with raw materials typically necessary to maintain conventional fasteners in a closed position during processes used to manufacturer disposable absorbent articles and the concomitant reduction in complications in the manufacturing processes. Furthermore, the improvements reduce the vulnerability of fastener elements to become damaged during processes, and especially high-speed processes, in which these articles are manufactured. Improvements also can include the provision of a fastener in a closed position that has a sufficiently strong closure bond such that the fastener remains in a closed position during the article's manufacturing process, yet sufficiently weak such that the article's user can readily handle the fastener and open it from its closed position for placement and fitting on the article's wearer.

Referring now to the drawings figures, wherein like reference numbers refer to the same or similar elements in the various figures, FIG. 1 is a partially cut-away perspective view of a disposable absorbent article (e.g., a diaper) 20 prior to its being placed on the diaper wearer (e.g., an infant) by the diaper user (e.g., a parent). As shown in FIG. 1, the article 20 includes a body portion 22 and a fastening system 24, which is described in more detail below. The body portion 22 includes a liquid pervious topsheet 26, an absorbent core 28, a liquid impervious backsheet 30, and leg cuffs 32 that include a side flap 34. In one embodiment, the leg cuffs are elastically contractible and, therefore, include one or more elastic members 36. The topsheet 26, the absorbent core 28, the backsheet 30, the side flaps 34, and the elastic members 36 may be assembled in a variety of well known disposable diaper configurations, such as, for example, those shown and described in Buell U.S. Pat. No. 3,860,003.

FIG. 1 shows an embodiment of the body portion 22 in which the topsheet 26 and the backsheet 30 are coextensive and have length and width dimensions generally larger than those of the absorbent core 28. The topsheet 26 is superposed on the backsheet 30 thereby forming a periphery 38 of the body portion 22. The periphery 38 defines the outer perimeter or, in other words, the outer extent of the body portion 22. The periphery 38 includes longitudinal edges 40 and end edges 42.

The body portion 22 has an inside surface 44 and an outside surface 46. In general, the outside surface 46 of the article 20 extends from one end edge 42 to the other end edge 42 of the diaper and from one longitudinal edge 40 to the other longitudinal edge 40 of the diaper and is the surface farthest from the wearer during use of the article 20. When a backsheet 30 is used, it typically forms the outside surface 46 of the body portion 22. The inside surface 44 is that surface of the article 20 opposite the outside surface 46 and, in the embodiment shown in FIG. 1, is typically formed by the topsheet 26. In general, the inside surface 44 of the article 20 is that surface coextensive with the outside surface 46, and which is for the greater part in contact with the wearer when the article 20 is worn. The inside surface 44 also is often referred to as the "body-facing" surface of the article 20, while the outside surface 46 is often referred to as the "garment-facing" surface.

The article 20 has first and second end regions 48 and 50, respectively, extending from the end edges 42 of the diaper periphery 38 toward the lateral centerline (denoted "LC" in FIG. 1) of the article 20. Both the first end region 48 and the second end region 50 extend a distance of about one-half of the length of the article 20 such that the end regions comprise each half of the article 20.

Both the first end region 48 and the second end region 50 have panels 52. The panels 52, also referred to herein as ear tabs, are those portions of the first end region 48 and the second end region 50 that overlap with one another when the article 20 is fastened about the waist of the wearer. The extent to which the end regions overlap and, thus, the extent to which the panels 52 are formed will depend on the overall dimensions and shape of the article 20 and the size of the article wearer.

The absorbent core 28 of the body portion 22 may be any material that is generally compressible, conformable, non-irritating to the wearer's skin, and capable of absorbing and retaining liquids and certain body exudates, such as urine or other fluids and fecal matter, discharged by an incontinent wearer of the article. The absorbent core 28 may be manufactured in a wide variety of sizes and shapes (e.g., rectangular, hourglass, T-shaped, asymmetric, etc.) and from a wide variety of liquid absorbent materials commonly used in disposable diapers and other disposable absorbent articles, such as comminuted wood pulp, generally referred to as airfelt, and comminuted and airlaid wood pulp, commonly referred to as absorbent fluff. Examples of other suitable absorbent materials include creped cellulose wadding, meltblown polymers, chemically-stiffened, modified, or cross-linked cellulosic fibers, tissue, absorbent foams including those prepared from polymerization of a high internal phase emulsion, absorbent sponges, superabsorbent polymers, absorbent gelling materials, or any other known absorbent materials or combination of materials. The total absorbent capacity of the absorbent core 28 should, however, be compatible with the design exudate loading in the intended use of the diaper 20. Further, the size and absorbent capacity of the absorbent core 28 may be varied to accommodate wearers ranging from infants to adults.

While the absorbent core 28 may include a single layer of absorbent material such as the configuration described in Weisman et al. U.S. Pat. No. 4,610,678, in one embodiment, the absorbent core 28 is a dual-layered absorbent core in a configuration such as is generally described in Weisman et al. U.S. Pat. No. 4,673,402, having an asymmetric-shaped upper layer 54 and a lower layer 56. According to one embodiment, the upper layer 54 acts as a liquid acquisition/distribution layer primarily constructed of hydrophilic fiber material. The lower layer 56 acts as a fluid storage layer containing a mixture of hydrophilic fiber material and particles of an absorbent gelling material (hydrogel material). Both the upper layer 54 and the lower layer 56 include an absorbent layer encased in a tissue layer. The size, shape, configuration, and total absorbent capacity of the upper layer 54 or the lower layer 56 may be varied to accommodate wearer's ranging from infants through adults. Therefore, the dimensions, shape, and configuration of both the upper layer 54 and the lower layer 56 may be varied (e.g., the upper layer 54 or the lower layer 56 may have a varying caliper, a hydrophilic gradient, a rapid acquisition zone or may contain absorbent gelling material).

The absorbent core 28 is superposed on the backsheet 30 and, in one embodiment, is associated thereto by a core attachment means 58, such as those well known in the art, for example, pressure-sensitive adhesives, hot melt adhesives or other adhesives; ultrasonic bonding; or heat/pressure sealing. The absorbent core 28 may be secured to the backsheet 30 by a uniform continuous layer of adhesive, a patterned layer of adhesive, or any array of separate lines or spots of adhesive. The core attachment means 58 can include an open pattern network of filaments of adhesive as is shown in Minetola et al. U.S. Pat. No. 4,573,986.

The backsheet 30 is impervious to liquids and, in one specific embodiment, is manufactured from a thin plastic film, although other flexible liquid impervious materials also may be used. The backsheet 30 prevents the liquids and exudates absorbed and contained in the absorbent core 28 from soiling garments that might contact the article 20, such as bed-sheets and undergarments. In one embodiment, the backsheet 30 is a polyethylene film having a thickness of from about 0.012 mm (0.5 mil) to about 0.051 mm (2.0 mils), although other flexible, liquid impervious materials may be used. As used herein, the term "flexible" refers to materials that are compliant and that will readily conform to the general shape and contours of the human body. The backsheet 30 may be embossed and/or matte-finished to provide a more cloth-like appearance. Further, the backsheet 30 may permit vapors to escape from the absorbent core 28 while still preventing liquids and exudates from passing through the backsheet 30. The size of the backsheet 30 generally will be determined by the size of the absorbent core 28 and the exact diaper design selected, for example. In one embodiment, the backsheet 30 has a modified hourglass shape extending beyond the absorbent core a minimum distance of at least about 1.3 cm to about 2.5 cm (about 0.5 to about 1.0 inch) around the entire diaper periphery 38.

The topsheet 26 of the body portion 22 is compliant, soft feeling, non-irritating (to the wearer's skin) planar material. Further, the topsheet 26 is liquid pervious, permitting liquids to readily penetrate through its thickness, and freely pass through it into the absorbent element. Its hydrophobic nature tends to cause its body-facing surface to be dryer and, therefore, protected from the fluids absorbed within the absorbent element. A suitable topsheet 26 may be manufactured from a wide range of materials such as porous foams, reticulated foams, apertured films, natural fibers (e.g., wood or cotton fibers), synthetic fibers (e.g., polyester or polypropylene fibers) or from a combination of natural and synthetic fibers. In one embodiment, the topsheet 26 is made of a hydrophobic material, such as a hydrophobic nonwoven fabric, to isolate the wearer's skin from liquids retained in the absorbent core 28. There are a number of manufacturing techniques that may be used to manufacture the topsheet 26. For example, the topsheet 26 may be woven, nonwoven, spunbonded, carded, hydroformed or the like.

The term "nonwoven fabric" means a web having a structure of individual fibers or threads which are interlaid, but not in a regular or identifiable manner as in a knitted fabric. Nonwoven fabrics or webs can formed from processes such as, for example, meltblowing processes, spunbonding processes, air laying processes, coforming processes, and bonded carded web processes.

Generally, and as used herein, the term "napped nonwoven," refers to a nonwoven fabric having a base nonwoven fabric and a layer of fibers on the surface of the base nonwoven fabric, wherein the layer of fibers has been raised up from the base nonwoven fabric to increase the loft of the nonwoven. The layer of fibers may be raised by one of a variety of methods including, but not limited to, brushing, beating, exposing to air from air jets, and the like.

The term "shedable nonwoven" refers to a nonwoven fabric having a base nonwoven fabric and a surface of fibers loosely bonded to the base nonwoven fabric. When the surface fibers are removed, the base nonwoven fabric typically retains about 70% or more of its tensile strength properties.

The term "spunbond," when referring to spunbound fibers, refers to a nonwoven fiber fabric of small diameter fibers that are formed by extruding a molten thermoplastic polymer into fibers from a plurality of capillaries of a spinneret. The extruded fibers are cooled to a non-tacky state while being drawn by an eductive or other well known drawing mechanism. The drawn fibers are deposited or laid onto a forming surface in a generally random, isotropic manner to form a loosely entangled fiber web, and then the laid fiber web is subjected to a bonding process to impart physical integrity and dimensional stability. The production of spunbond fabrics is disclosed, for example, in Dorschner et al. U.S. Pat. No. 3,692,618, Matsuo et al. U.S. Pat. No. 3,802,817, and Appel et al. U.S. Pat. No. 4,340,563. Typically, spunbond fibers have a linear density of about 2 denier to about 6 denier and a diameter of about 10 µm to about 30 µm (for example about 15 µm to about 25 µm), although finer and heavier spunbond fibers can be produced.

According to one embodiment, the topsheet is carded and thermally bonded by means well known to those skilled in the fabric art. Consistent with that embodiment, the topsheet 26 can have a basis weight from about 15 grams per square meter ($g/m^2$) to about 30 $g/m^2$, a minimum dry tensile strength of at least about 400 grams per centimeter (g/cm) in the machine direction and a wet tensile strength of at least about 55 g/cm in the cross-machine direction. In another embodiment, the topsheet 26 is spun-bonded nonwoven polyester fabric made from fibers of from about 2.2 to about 2.5 denier, having a basis weight of about 17 $g/m^2$. In yet another embodiment, the topsheet 26 includes about 65% staple length, 1.5 denier polyester fibers; about 15% crimped, staple length, 1.5 denier rayon fibers; and about 20% acrylic copolymer binder. In still another embodiment, the topsheet 26 includes staple length polypropylene fibers having a denier of about 1.5. As used herein, the term "staple length fibers" refer to those fibers having a length of at least about 15.9 mm (0.625 inches).

The topsheet 26 and the backsheet 30 are associated together in any suitable manner as is well known in the diaper manufacturing art. As used herein, the term "associated" encompasses configurations whereby the topsheet 26 is directly joined to the backsheet 30 by affixing the topsheet 26 directly to the backsheet 30, and configurations whereby the topsheet 26 is indirectly joined to the backsheet 30 by affixing the topsheet 26 to intermediate members which in turn are affixed to the backsheet 30. In one embodiment, the topsheet 26 and the backsheet 30 are joined directly to each other in the diaper periphery 38 by a flap attachment means 60 such as an adhesive or any other attachment means as is known in the art. In general, the core attachment means 58 that affixes the absorbent core 28 to the backsheet 30 is the same means as the flap attachment means 60 that affixes the topsheet 26 to the backsheet 30. Thus, for example, a uniform continuous layer of adhesive, a patterned layer of adhesive, an array of separate lines or spots of adhesive, or a network or adhesive filaments such as shown in U.S. Pat. No. 4,573,986 may be used.

Leg cuffs 32, such as elastically contractible leg cuffs, are disposed adjacent the periphery 38 of the body portion 22, such as along each longitudinal edge 40, so that the leg cuffs 32 tend to draw and hold the article 20 against the legs of the wearer. While the leg cuffs 32 may include any of several means as are well known in the diaper art, one specific embodiment of the leg cuff construction includes a side flap 34 and one or more elastic members 36, as is described in detail in Buell U.S. Pat. No. 3,860,003. Additionally, a method and apparatus suitable for manufacturing a disposable diaper having elastically contractible leg cuffs are described in Buell U.S. Pat. No. 4,081,301, Lawson U.S. Pat. No. 4,695,278, Dragoo U.S. Pat. No. 4,795,454, and Buell U.S. Pat. No. 4,900,317. In another embodiment, the elastically contractible leg cuff 32 includes a side flap 34 and an elastic member 36 including an elastic thread.

The article (diaper) 20 is provided with a fastening system (one embodiment of which is generally designated 24 in FIG. 1) for forming a side closure. The fastening system generally includes a fastener 62 and a landing member 64 for receiving the fastener, and various embodiments of these elements of the fastener are described below with reference to the other drawing figures. The diaper 20 is fitted to the wearer and the first end region 48 and the second end region 50 are maintained in an overlapping configuration by the fastening system 24 when the diaper 20 is worn. As described in more detail below, embodiments of the fastener 62 are intended to engage the landing member 64 so as to provide a secure side closure for the diaper 20 when worn by the diaper wearer.

The fastener 62 is fixed to the article 20 and is positioned on the outside surface 46 of the body portion 22 in the panels (ear tabs) 52 in the first end region 48, one adjacent each longitudinal edge 40, so as to engage the landing member 64 disposed in the second end region 50. The fastener 62 is fixed to the body portion 22 and, in one embodiment, covers an area about 1 inch wide (i.e., generally perpendicular to longitudinal centerline (designated "LC" in FIG. 1)) by about 2.5 inches long (i.e., generally parallel to the longitudinal centerline) at the panels 52 of the body portion 22.

As described in more detail below, the various embodiments of the fastener may generally be considered either as being out-board of the article periphery when the fastener is in a closed position or in-board of the article periphery when in the closed position. FIGS. 2A through 3C describe fasteners that remain in-board of the article periphery when closed, whereas FIGS. 4A through 6C describe fasteners remaining out-board of the article periphery when closed. Each embodiment realizes one or more improvements over conventional fastener designs.

Figure 2A:
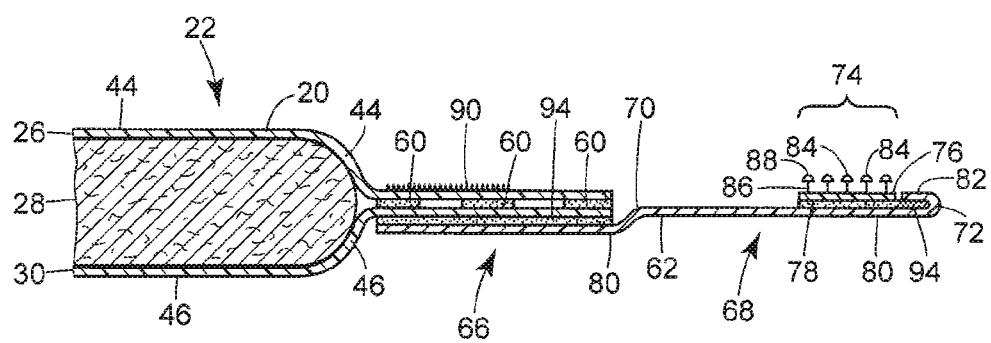
FIG. 2A is a cross-sectional view of the upper right-hand corner of the diaper of FIG. 1, the view illustrating one embodiment of a fastener in an "open" position.
Figure 2B:
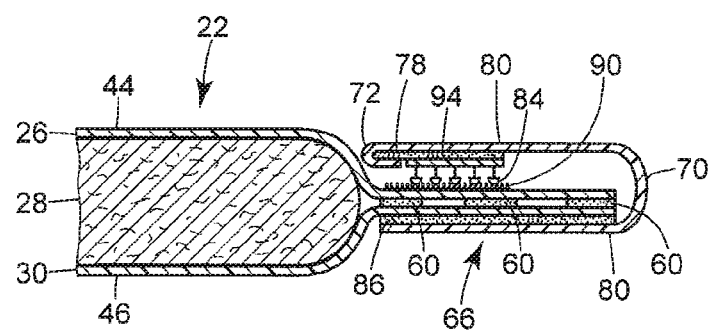
FIG. 2B is a cross-sectional view of the fastener of FIG. 2A in a "closed" position.
Figure 2C:
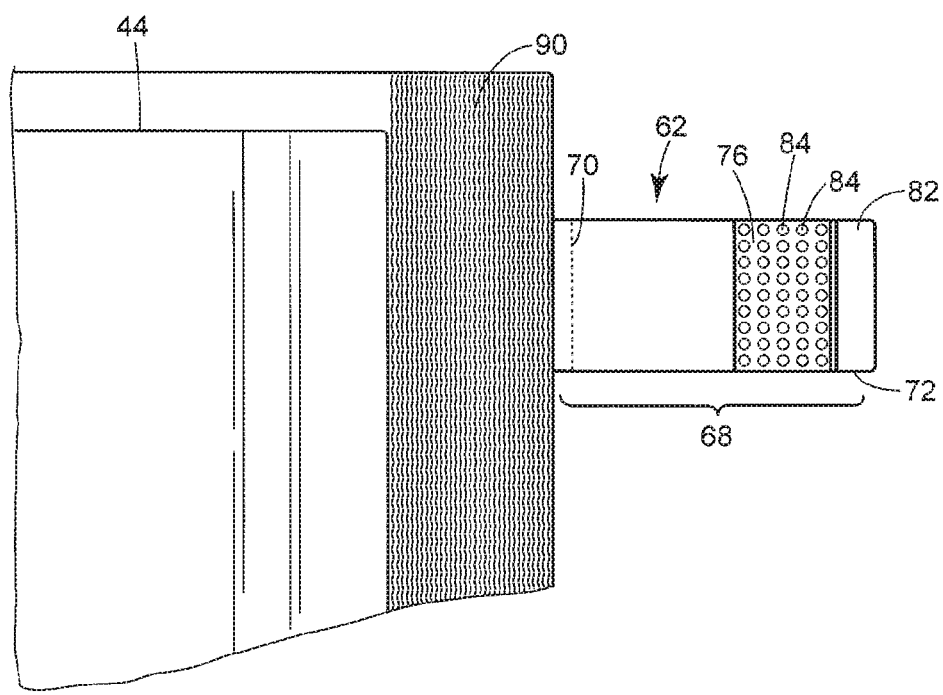
FIG. 2C is a top plan view of the fastener of FIG. 2A.

With reference to FIGS. 2A through 2C, the fastener 62 is free of a release tape and includes a fixed portion 66 attachable (and shown as attached) to the article 20, a connective portion 68 joined to and contiguous with the fixed portion 66, and a folding line 70 disposed between the fixed and connective portions 66 and 68, respectively. The connective portion 68 includes a distal edge 72. The connective portion 68 also includes a fastening member 74 having a fastening surface 76 and a bonding surface 78 opposite to the fastening surface 76, wherein the fastening surface 76 is releasably fastenable to a portion of the article 20, in certain embodiments, to the landing member 64 of the article 20 and also a layer 90 of napped nonwoven fabric on the article adjacent the fastener. The connective portion 68 also includes a backing member 80 attached to the bonding surface 78 of the fastening member 74.

The connective portion 68 of the fastener 62 may also include a grip tab 82 disposed adjacent to and between the fastening member 74 and the distal edge 72. The grip tab 82 may be formed by folding over a small margin of the distal edge 72 of the connective portion 68 and attaching it to itself. This forms an end on the connective portion 68 that may be easier to grasp by the diaper user when the diaper 20 is to be fitted and attached to the wearer.

As shown in FIGS. 2A and 2B, the fastening member 74 may include a plurality of engaging elements 84 outwardly extending from the fastening surface 76. As shown, each engaging element 76 includes a stem 86 supported at one end by the fastening surface 76 and a head 88 disposed at the stem 86 end opposite the fastening surface 76.

FIG. 2B is a cross-sectional view of the fastener of FIG. 2A shown in a "closed" position, for example, prior to the article's use by the diaper wearer. In FIG. 2B, the connective portion 68 is folded along the folding line 70 onto a portion of the article 20 to permit the fastening member 74 to releasably fasten to the article 20. Specifically, and as shown in FIG. 2B, the portion of the article 20 onto which the connective portion 68 is folded includes a layer 90 of napped nonwoven fabric. The layer 90 of napped nonwoven fabric can complementarily engage the engaging elements 84 on the fastening member 74. When ready for use, the fastening member 74 may be disengaged from the layer 90 of napped nonwoven fabric.

FIG. 2C is a top plan view of the fastener illustrated in FIGS. 2A and 2B. In FIG. 2C, however, the fastener 62 is shown in an "open" position (as it is in FIG. 2A).

With continued reference to FIGS. 2A and 2B, the fixed portion 66 of the fastener 62 is fixed to the outside surface 46 of the body portion 22 to create a manufacturer's end (i.e., that attachment of the fastener 62 to the diaper 20 made during manufacture of the diaper 20). The connective portion 68 is that portion of the fastener 62 releasably fastenable to the landing member 64 by the user when securing the diaper 20 on the wearer, and releasably fastenable to the layer 90 of napped nonwoven fabric when manufactured, shipped and stored prior to use. The connective portion 68, thus, forms the user's end as it is manipulated by the user to open the fastener 62 from its closed position, and to secure it to the landing member 64, thereby securing the diaper 20 to the wearer. Additionally, the outer surface of the fixed portion 66 and the outer surface of the connective portion 68 form the backing member 80 of the fastener 62. A portion of the backing member 80 is bonded to the bonding surface 78 of the fastening member 74.

The fixed portion 66 and the connective portion 68 can each be separate tapes which meet and are joined adjacent the longitudinal edge 40 of the body portion 22 in an area of joinder. However, a more practical structure for the fastener 62 is one in which the connective portion 68 and the fixed portion 66 are a unitary strip of tape material.

FIGS. 2A and 2B also show fastener attachment means 94 for fixing the fastener 62 to the body portion 22. These fastener attachment means 94 are any of those attachment means capable of providing an adequate bond, such as, for example, heat bonds, pressure bonds, ultrasonic bonds, dynamic mechanical bonds, or any other suitable attachment means or combinations of these attachment means as are known to those of ordinary skill in the art. The fastener attachment means 94 may include any of those adhesives capable of providing an adequate bond with other portions of the diaper, and is, in one specific embodiment, a pressure-sensitive adhesive such as code number XPF 1.42.34 available from The 3M Company (St. Paul, Minn.). In one embodiment, the fastener attachment means is an ultrasonic bond. Suitable methods for ultrasonic bonding are described in Schaefer U.S. Pat. No. 4,430,148 and Willhite, Jr. et al. U.S. Pat. No. 4,823,783. Suitable equipment for ultrasonic bonding is available from Branson Ultrasonics Corporation of (Danbury, Conn.). High-pressure or ultrasonic bonding has been found to suitably fix the fastener to the article, especially, where the fastener is being attached to a layer of nonwoven fabric (e.g., spunbond-meltblown-spunbond (SMS) fibers) on the article.

As shown and described above, the inner surface of the fixed portion 66 is affixed to the outside surface 46 of the body portion 22 by a fastener attachment means 94. The connective portion 68 is provided with a fastening member 74 joined to it by another fastener attachment means 94, although an adhesive attachment means may be placed on the fastening member 74 separately and the combined material joined to the connective portion 68.

Materials for the fastener can include a tape material such as tape code numbers XPF 14.43.0, Y-9376, or Y-9030 available from The 3M Company (St. Paul, Minn.). The tape materials in the various embodiments disclosed herein are a polyethylene film having a fastener attachment means tailored to bond to the polyethylene positioned on the tape material.

The fastening member 74 of the fastener 62 forms a closure between the fastener 62 and the landing member 64. More specifically, the engaging elements 84 of fastening member 74, in one embodiment, engage a complementary fastening surface 92 of the landing member 64 to maintain the first end region 48 and the second end region 50 in an overlapping configuration to provide a secure side closure. As discussed in more detail below, the fastening surface 92 may include any of the well known means for achieving a closure such as buttons, snaps, hook fastening materials, or loop fastening materials. In one specific embodiment, however, the fastening surface 92 includes loop fastening materials. As used herein, the term "hook fastening material" is used to designate a material having engaging elements 84. The hook fastening material may also be referred to as a male fastener. It should also be understood that the use of the term "hook" should be non-limiting in the sense that the engaging elements 84 may comprise any shapes as are known in the art so long as they are adapted to engage a complementary fastening surface 92 of the landing member 64, for example. The hook fastening materials are intended to engage fibrous elements of a loop fastening material so as to provide a secure fastening system. Thus, the hook fastening material may be manufactured from a wide range of materials. Suitable materials include nylon, polyester, polypropylene, or any combination of these materials. A suitable hook fastening material includes a number of shaped engaging elements 84 projecting from a woven backing such as the commercially available material designated "Scotchmate" brand No. FJ3402 available from The 3M Company (St. Paul, Minn.). Alternatively, the engaging elements may have any shape such as hooks, "T's" or any other shape as are well known in the art. A suitable hook fastening material is described in Scripps U.S. Pat. No. 4,846,815.

The fastening member 74 may be a separate member fixed to and associated with the fastener 62 or a unitary member with the fastener 62. The fastening member 74 may be directly attached to the connective portion 68 or may be indirectly attached to the connective portion 68, such as by attaching the fastening member 74 to an intermediate member which, in turn, is attached to the connective portion 68. In one embodiment, as shown in FIGS. 2A and 2B, the fastening member 74 is directly fixed to the connective portion 68 of the fastener 62 by the fastener attachment means 94. The fastener 62 may be positioned in the panels (also referred to as ear tabs) 52 of the first end region 48 adjacent the longitudinal edges 40. The fastening member 74 may be positioned either on all of or at least a portion of the connective portion 68. In a further embodiment, the fastening member 74 may be disposed on a first area (or portion) of the connective portion 68 adjacent the distal edge 72 of the fastener 62.

The landing member 64 of the fastening system 24 provides a means for securing itself and the fastener 62 together to provide a secure side closure and to maintain the first end region 48 and the second end region 50 in an overlapping configuration. The landing member 64 may be disposed anywhere on the diaper 20 so long as it engages the fastener 62 to provide the side closure. For example, the landing member 64 may be disposed on the outside surface 46 in the second end region 50 (as shown in FIG. 1), or on any other portion of the diaper 20 which is disposed to engage the fastener 62. In addition, the landing member 64 may be a unitary piece of material that is neither divided nor discontinuous with an element of the diaper 20 such as the topsheet 26 or the backsheet 30. While the landing member 64 can assume varying sizes and shapes, one embodiment of the diaper 20 illustrated in FIG. 1 can have a shaped landing member 64 secured to the outside surface 46 of the body portion 22 in the panels (ear tabs) 52 of the second end region 50 adjacent each of the longitudinal edges 40.

The landing member 64 may include a fastening surface 92 engageable with the fastening member 74 of the fastener 62. Thus, the fastening surface 92 may be manufactured from a wide range of materials and configurations capable of securely engaging the fastening member 74. For example, the fastening surface 92 may include identical complementary elements with the fastening member 74 or distinct complementary elements with the fastening member 74. As used herein, the term "identical complementary elements" is used to define mechanical fastening systems wherein the engaging elements 84 of the fastening member 74 and the fastening surface 92 comprise the same configuration or structure that are interlocking. Examples of such systems are described in Brown et al. U.S. Pat. No. 4,322,875 and Kellenberger et al. U.S. Pat. No. 4,701,179. The term "distinct complementary elements" is used herein to designate a system wherein the fastening member 74 is different from the fastening surface 92 but is engageable therewith such as buttons and holes, a hook fastening material and a loop fastening material, or a male member and a female member. The fastening surface 92 can include a hook fastening material or a loop fastening material depending upon whether the fastening member 74 is a loop fastening material or a hook fastening material. As shown in FIG. 1, the landing member 64 can include a fastening surface 92 having a plurality of fiber elements such as a loop fastening material 94.

In one embodiment, the loop fastening material of the landing member 64 can provide a plurality of fiber elements that engage the engaging elements 84 of the fastening member 74 (hook fastening material). The loop fastening material may be manufactured from a wide range of materials to provide fiber elements, such as loops. Such suitable materials include nylon, polyester, polypropylene, or any combination of these materials. A suitable loop fastening material 94 includes a number of fiber loops projecting from a woven backing such as the commercially available material designated "Scotchmate" brand nylon woven loop No. SJ3401 available from The 3M Company (St. Paul, Minn.). In one embodiment, the loop fastening material includes a tricot knit fabric having a plurality of nylon filament loops projecting from a backing of nylon such as the commercially available material designated "Guilford No. 16110" available from Guilford Mills (Greensboro, N.C.). In an alternative embodiment, the loop fastening material may be a nonwoven fabric or any other type of fiber material or loop material well known in the art. An inexpensive loop fastening material and a method of making such a loop fastening material is described in Noel et al. U.S. Pat. No. 5,032,122.

In use, the diaper 20 is applied to the wearer by positioning the first end region 48 under the wearer's back and drawing the remainder of the diaper 20 between the legs of the wearer so that the second end region 50 is positioned across the front of the wearer. The connective portion 68 of the fastener 62 is then positioned adjacent to the landing member 64 positioned on the outside surface 46 of the second end region 50 so that the fastening member 74 which is disposed on the fastener 62 will engage the fastening surface 92 of the landing member 64 to form a side closure. After the diaper 20 has been soiled, the diaper 20 is removed from the wearer. The diaper 20 is then folded or rolled up into a configuration for disposal. In rolling up the diaper 20, the panels 52 in the second end region 50 are in-folded, and the body portion 22, beginning with the second end region 50, is rolled into a structure with the fastener 62 extending outwardly from the rolled-up diaper 20. The fastening member 74 of the fastener 62 is then secured to the diaper 20 (and, in one embodiment, to the outside surface 46 thereof) so as to secure the diaper 20 in its rolled-up configuration so that it may be easily and conveniently disposed in a waste receptacle.

Figure 3A:
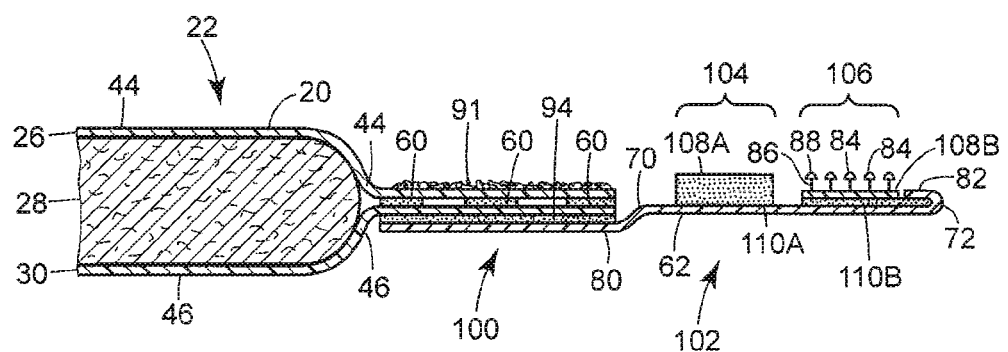
FIG. 3A is a cross-sectional view of a corner of the diaper illustrating an alternative embodiment of the fastener in an "open" position.
Figure 3B:
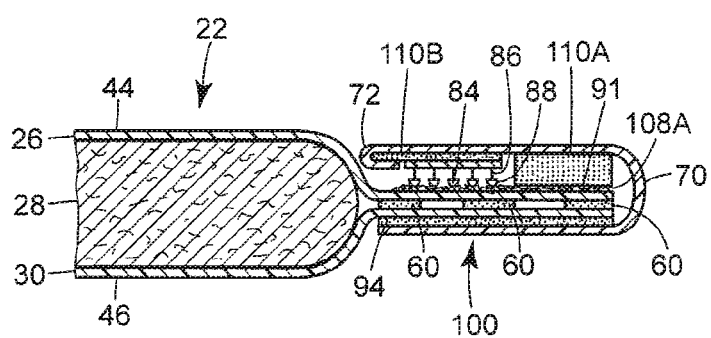
FIG. 3B is a cross-sectional view of the fastener of FIG. 3A in a "closed" position.
Figure 3C:
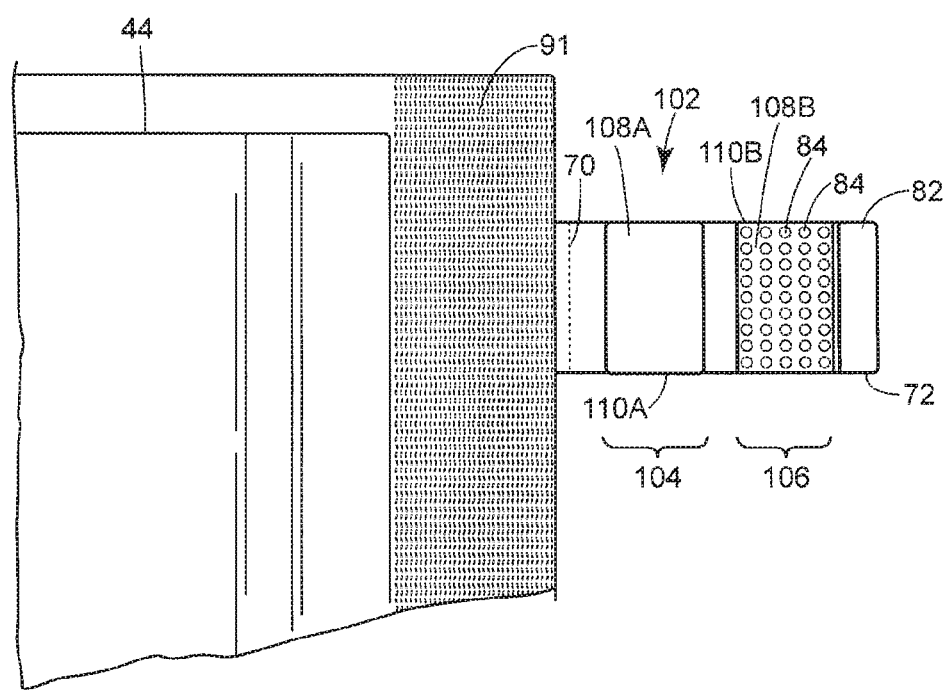
FIG. 3C is a top plan view of the fastener of FIG. 3A.

Alternative embodiments of the fastener are shown in the remaining drawing figures. For example, FIGS. 3A through 3C show a release tape free fastener 62 that includes a fixed portion 100 attachable (and shown attached to) the article 20, a connective portion 102 joined to and contiguous with the fixed portion 100, and a folding line 70 disposed between the fixed and connective portions (100 and 102, respectively). As shown, the connective portion 102 includes a fastening member defined by dissimilar proximate and distal fastening members (104 and 106, respectively). The proximate fastening member 104 includes a fastening surface 108A and a bonding surface 110A opposite to the fastening surface 108A. The distal fastening member 106 includes a fastening surface 108B and a bonding surface 110B opposite to the fastening surface 108B. At least one of these fastening surfaces is fastenable to a layer of shedable nonwoven fabric on the article 20. More specifically, and as shown in FIGS. 3A and 3B, at least one of the fastening surfaces 108A and 108B is fastenable to a layer 91 of shedable nonwoven fabric disposed on the portion of the article 20 adjacent the folding line 70 of the fastener 62.

As shown, the distal fastening surface 106 includes a plurality of engaging elements 84 outwardly extending from the distal fastening surface 108B. Each engaging element 84 includes a stem 86 supported at one end by the distal fastening surface 108B and a head 88 disposed at the stem 86 end opposite the distal fastening surface 108B.

The proximate and distal fastening surfaces are not limited to the embodiments depicted in FIGS. 3A through 3C. Accordingly, in the embodiment shown in these figures, the proximate fastening surface is fastenable to the layer of shedable nonwoven fabric. The proximate fastening surface is an adhesive, and may be an adhesive capable of adhering to the shedable nonwoven fabric for a time sufficient to maintain the fastener in a closed position (shown in FIG. 3B) during the manufacturing process. Where the proximate fastening surface is an adhesive, the fastener includes a plurality of engaging elements outwardly extending from the distal fastening surface. Each of these engaging elements includes a stem supported at one end by the distal fastening surface and a head disposed at the stem end opposite the distal fastening surface. Accordingly, the distal fastening surface is releasably fastenable to a landing member on the article.

Alternatively, the distal fastening surface may be fastenable to the layer of shedable nonwoven material. In this alternative embodiment (not shown), the distal fastening surface is an adhesive and, in certain embodiments, an adhesive capable of adhering to the shedable nonwoven material for a time sufficient to maintain the fastener in a closed position during the manufacturing process. Where the distal fastening surface is an adhesive, the fastener includes a plurality of engaging elements outwardly extending from the proximate fastening surface. Each of these engaging elements includes a stem supported at one end by the distal fastening surface and a head disposed at the stem end opposite the distal fastening surface. Accordingly, in this alternative embodiment (not shown), the proximate fastening surface is releasably fastenable to a landing member on the article.

FIG. 3B is a cross-sectional view of the fastener 62 shown in a "closed" position as it may be prior to the article's use, for example. In FIG. 3B, the connective portion 102 (including the proximate and distal fastening surfaces 108A and 108B, respectively) is folded along the folding line 70 onto the layer 91 of shedable nonwoven fabric disposed on the portion of the article 20 adjacent the folding line 70 of the fastener 62. The layer 91 of shedable nonwoven fabric may complementarily engage the engaging elements on the distal fastening surface 108B while also adhering to the adhesive of the proximate fastening surface 108A. These fastening surfaces (108A and 108B) therefore ensure that the fastener 62 is maintained in a closed position until the article 20 is ready for use.

When ready for use, the fastening surfaces (108A and 108B) may be disengaged from the layer 91 of shedable nonwoven fabric on the article 20. Fibers from the shedable nonwoven material may desirably remain adhered to the adhesive of the proximate fastening surface 108A and, thereby weaken the strength of the adhesive. This strength-weakening is desirable, for example, because the adhesive will be less likely to undesirably stick to the wearer's skin or to the user's hand during times when the article 20 is being handled for attachment to the wearer or for disposal. When the fastening surfaces are disengaged from the layer 91 of shedable nonwoven fabric and laid in the open position (as shown in FIGS. 3A and 3C), the fastener 62 and, more specifically, the engaging elements 84 of the distal fastening surface 108B, can engage the fastening surface 92 of the landing member 64 so as to provide a suitable side closure.

In the embodiment shown in FIGS. 3A through 3C, the proximate fastening surface 108A includes an adhesive. In an alternative embodiment (not shown), however, the distal fastening surface may include the adhesive, while the proximate fastening surface may include the fastening elements.

Suitable adhesives for maintaining the fastener (shown in FIGS. 3A through 3C) in a closed position include adhesives that are capable of providing a temporary bond having a peel strength and shear strength sufficient to maintain the fastener in a closed position during the article's manufacturing process, but weak enough to permit the article's user to readily open the fastener when the article is ready for use. In one embodiment, the adhesive is capable of providing a bond having strength sufficient to maintain the fastener in a closed position during the article's manufacturing process, which bond approaches zero strength when the article's user removes the article from its packaging. To provide a suitable bond, a low basis weight of adhesive may be used as the adhesive. The adhesive may be a pressure-sensitive adhesive such as code number XPF 1.42.34 available from The 3M Company (St. Paul, Minn.). This type of bond can be provided by a variable coating or printing process capable of minimizing the amount of adhesive used or to print the adhesive in a tapered pattern such that the adhesive enables easy peel by the article's user. Accordingly, the bond will resist drag forces commonly encountered during the article's manufacturing process; but, offers desirably little resistance when the article's user attempts to peel the fastener open. Still, another alternative would be to use an adhesive that has sufficient tack (wet) strength when applied to the fastener and when the fastener is initially closed, but loses that tack strength (dries) shortly thereafter. Solvent-, water-, and starch-based adhesives may be suitable for this purpose.

FIG. 3C is a top plan view of the fastener illustrated in FIGS. 3A and 3B. In FIG. 3C, the fastener 62 is shown in an "open" position (as in FIG. 3A).

FIGS. 4A through 6C illustrate fastener embodiments where the fastener, in its closed position, remains outboard of the article's periphery 38. Generally, these fastener embodiments include a fixed portion attachable to the article, and a connective portion joined to and contiguous with the fixed portion. The connective portion includes a distal edge, and proximate and distal fastening members. Each of these fastening members includes a fastening surface and a bonding surface opposite to the fastening surface, wherein the fastening surfaces are releasably fastenable to each other. The connective portion also includes a backing member attached to the bonding surfaces of the proximate and distal fastening members. In addition to the fixed and connective portions, the fastener includes a folding line disposed on the connective portion between the proximate and distal fastening members.

The embodiments of the fastener illustrated in FIGS. 4A through 6C provide certain processing advantages over those described relative to FIGS. 2A through 3C. Specifically, the former are advantageous in that the fasteners can be folded into a closed position prior to being fixed to the article. In other words, the fasteners can be provided to and fixed to the article in a high-speed article manufacturing process while already in a closed position. This design, therefore, avoids or minimizes, the potential for fastening elements on the fastener to become damaged during the high-speed article manufacturing process because the fastener is maintained in a closed position for longer periods of the process. The embodiments shown in FIGS. 2A through 3C, in contrast, typically will require the article's manufacturer to provide and fix those fastener embodiments to the article while the fastener is in the open position and, thereafter, require the article's manufacturer to include processing steps to fold the fastener into a closed position. Fixing the fastener to the article while the fastener is in the open position as well as the additional processing steps provide the possibility that fastener elements may become damaged by the article manufacturing process—a possibility that is avoided or minimized by the fastener embodiments illustrated in FIGS. 4A through 6C.

In various embodiments described in more detail below with reference to the drawing FIGS. 4A through 6C, these fasteners can include, for example, a plurality of engaging elements outwardly extending from the fastening surface of the distal fastening member. Each of these engaging elements includes a stem supported at one end by the fastening surface of the distal fastening member and a head disposed at the stem end opposite the fastening surface of the distal fastening member. When the distal fastening surface includes these fastening members, the fastening surface of the proximate fastening member may be selected from the group consisting of an adhesive, a napped nonwoven fabric, and combinations thereof. The fastening surface of the distal fastening member is releasably fastenable to a landing member on the article. In contrast, however, the fastening surface of the proximate fastening member is not releasably fastenable to the landing member on the article.

Alternatively, the features of the distal and proximate fastening surfaces described in the preceding paragraph may be reversed relative to the two fastening surfaces. For example, the fastener can include a plurality of engaging elements outwardly extending from the fastening surface of the proximate fastening member. Each of these engaging elements includes a stem supported at one end by the fastening surface of the proximate fastening member and a head disposed at the stem end opposite the fastening surface of the proximate fastening member. When the proximate fastening surface includes these fastening members, the fastening surface of the distal fastening member may be selected from the group consisting of an adhesive, a napped nonwoven fabric, and combinations thereof. Accordingly, the fastening surface of the proximate fastening member is releasably fastenable to a landing member on the article, whereas the fastening surface of the distal fastening member is not releasably fastenable to the landing member on the article.

Figure 4A:
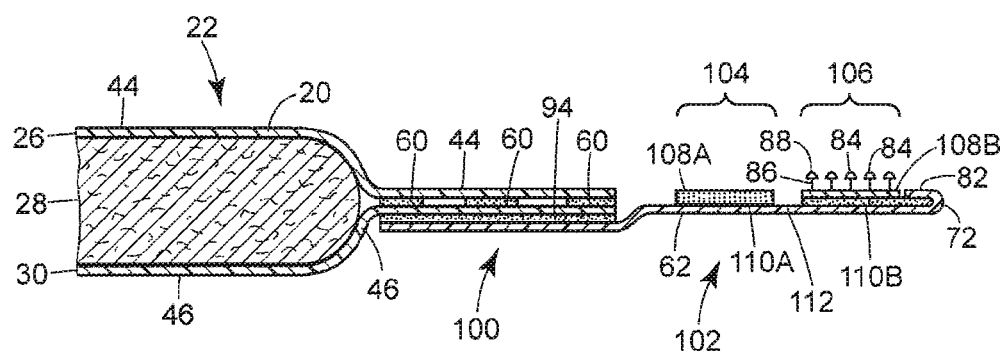
FIG. 4A is a cross-sectional view of a corner of the diaper illustrating an alternative embodiment of the fastener in an "open" position.
Figure 4B:
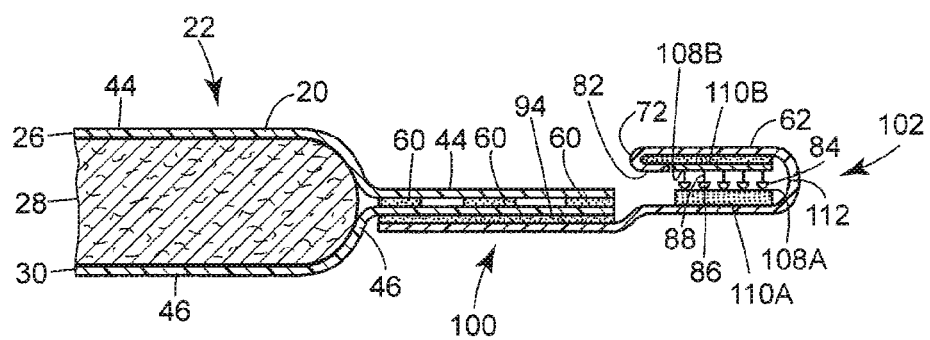
FIG. 4B is a cross-sectional view of the fastener of FIG. 4A in a "closed" position.
Figure 4C:
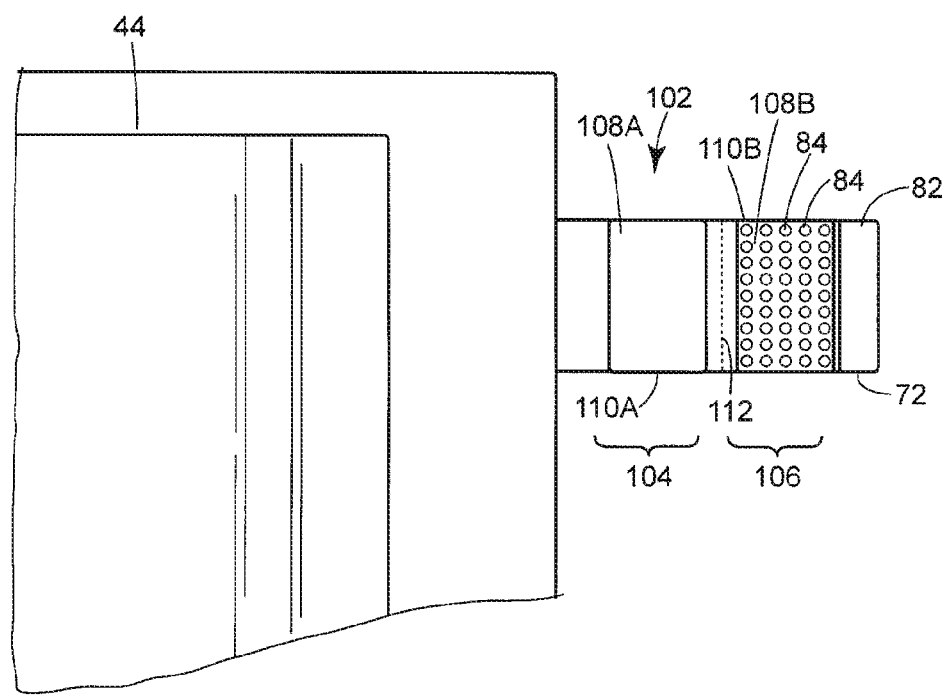
FIG. 4C is a top plan view of the fastener of FIG. 4A.

A fastener embodiment shown in FIGS. 4A through 4C is similar to the embodiment shown in FIGS. 3A through 3C. Notably different in this embodiment, however, is that the fastener 62 in FIGS. 4A through 4C includes a folding line 112 between the proximate fastening member 104 and the distal fastening member 106. With this modification, the fastening surfaces 108A and 108B are releasably fastenable to each other, as shown in FIG. 4B. Specifically, when the proximate fastening surface 108A is an adhesive, that surface 108A is capable of suitably adhering to the engaging elements 84 of the distal fastening surface 108B. Accordingly, the article need not (and does not in FIGS. 4A through 4C) contain a layer of napped nonwoven fabric because the fastening surfaces 108A and 108B need not engage the article 20 to maintain the fastening surfaces 108A and 108B in a "closed" position prior to the article's use.

When ready for use, the fastening surfaces (108A and 108B) may be disengaged from one other by the user. When these surfaces are disengaged from one another and laid in the "open" position (as shown in FIGS. 4A and 4C), the fastener 62 and, more specifically, the engaging elements 84 of the distal fastening surface 108B, can engage the fastening surface 92 of the landing member 64 so as to provide a suitable side closure.

The embodiment shown in FIGS. 4A through 4C is advantageous in that only low peel forces are required to open the fastener when the article is ready for use. The low peel force may be attributed to the surface area of heads on the fastening surface that engage the adhesive. Adhesives suitable for use as a fastening surface in the embodiment shown in FIGS. 4A through 4C include those discussed above relative to the embodiment shown in FIGS. 3A through 3C. Generally, the adhesive should be capable of providing a temporary bond having a peel strength and shear strength sufficient to maintain the fastener in a closed position during the article's manufacturing process, but weak enough to permit the article's user to readily open the fastener when the article is ready for use. In one embodiment, the adhesive is capable of providing a bond having strength sufficient to maintain the fastener in a closed position during the article's manufacturing process, which bond approaches zero strength when the article's user removes the article from its packaging.

Figure 5A:
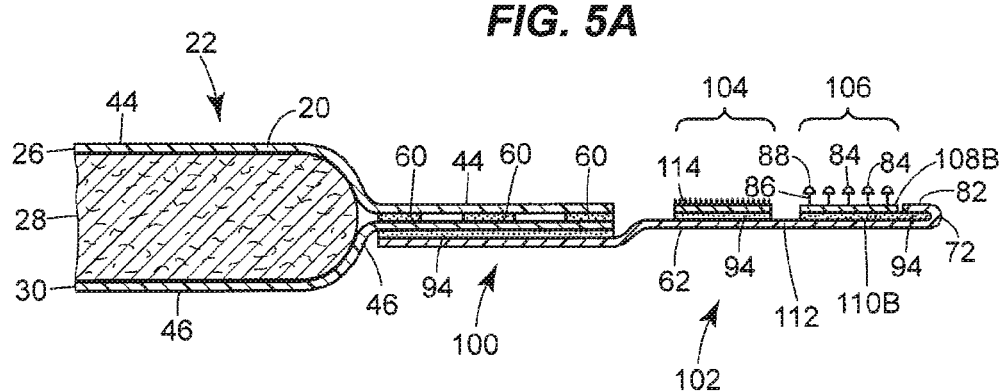
FIG. 5A is a cross-sectional view of a corner of the diaper illustrating an alternative embodiment of the fastener in an "open" position.
Figure 5B:
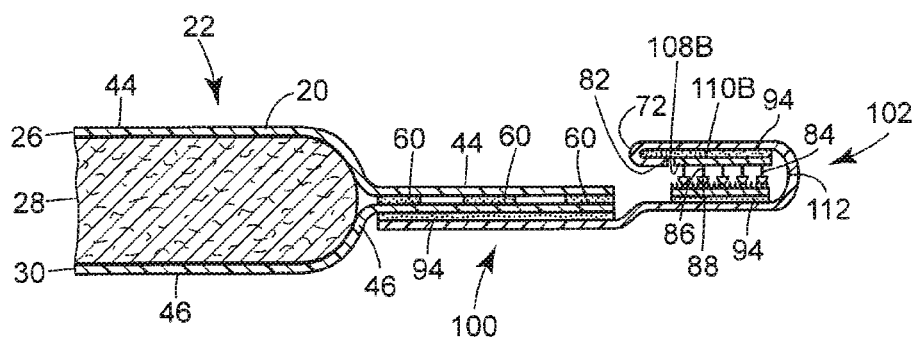
FIG. 5B is a cross-sectional view of the fastener of FIG. 5A in a "closed" position.
Figure 5C:
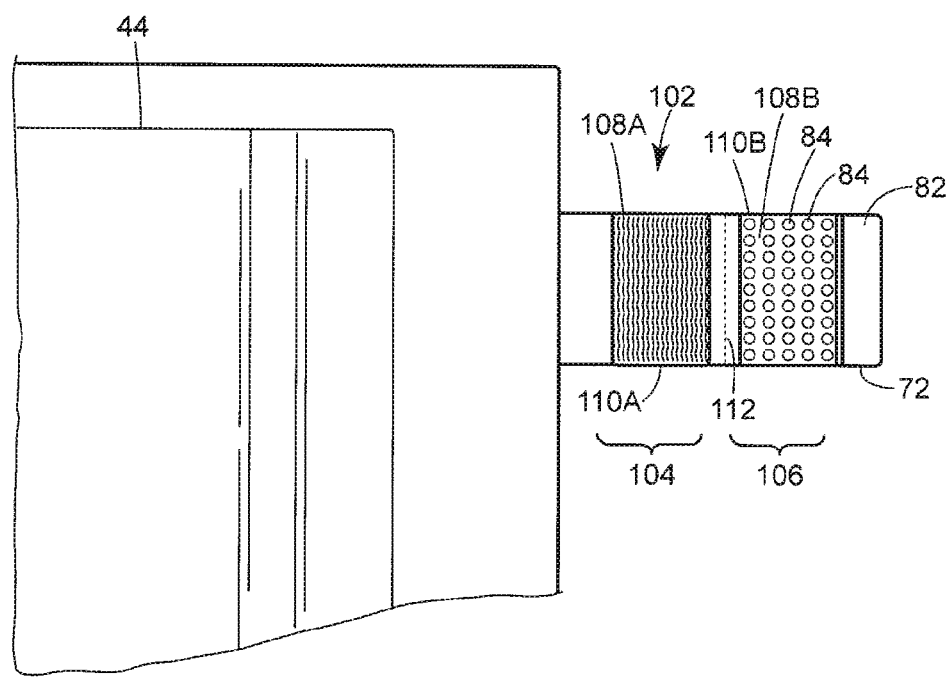
FIG. 5C is a top plan view of the fastener of FIG. 5A.

FIGS. 5A through 5C illustrate yet another embodiment of a suitable fastener. This embodiment is similar to the one shown in FIGS. 4A through 4C. The fastener 62 shown in FIGS. 5A through 5C, however, includes a proximate fastening member 104 that is a napped nonwoven fabric or a layer 114 of napped nonwoven fabric. This layer 114 of napped nonwoven fabric is affixed to the connective portion 102 by the fastener attachment means 94 described above.

In the embodiment shown in FIGS. 5A through 5C, the distal fastening surface 108B and, more specifically, the engaging elements 84 of the distal fastening surface 108B, releasably engage the layer 114 of napped nonwoven fabric (as shown in FIG. 5B). When ready for use, the fastening surface 108B may be disengaged from the layer 114 of napped nonwoven fabric by the user and laid in the "open" position (as shown in FIGS. 5A and 5C). In the open position, the engaging elements 84 of the distal fastening surface 108B can engage the fastening surface 92 of the landing member 64 so as to provide a suitable side closure.

The embodiment shown in FIGS. 5A through 5C is advantageous in that it eliminates the use of an adhesive to maintain the fastener in a closed position. By eliminating the necessity of the adhesive, the manufacturer may realize cost savings relative to the cost typically associated with the use of the adhesive. Furthermore, the elimination of the adhesive avoids the potential for the fastener to undesirably stick to the skin of the article's wearer (e.g., an infant) or to the hands of the article's user (e.g., a parent) when placing the article on the wearer.

Generally, the nonwoven fabric is brushed to loft or otherwise raise fibers comprising the fabric from the surface such that fastening elements on the fastener can releasably engage the fabric and provide a temporary bond having a peel strength and shear strength sufficient to maintain the fastener in a closed position during the article's manufacturing process, but weak enough to permit the article's user to readily open the fastener when the article is ready for use. In one embodiment, the napped nonwoven fabric when engaged with the fastening elements on the fastener is capable of providing a bond having strength sufficient to maintain the fastener in a closed position during the article's manufacturing process, which bond approaches zero strength when the article's user removes the article from its packaging.

Figure 6A:
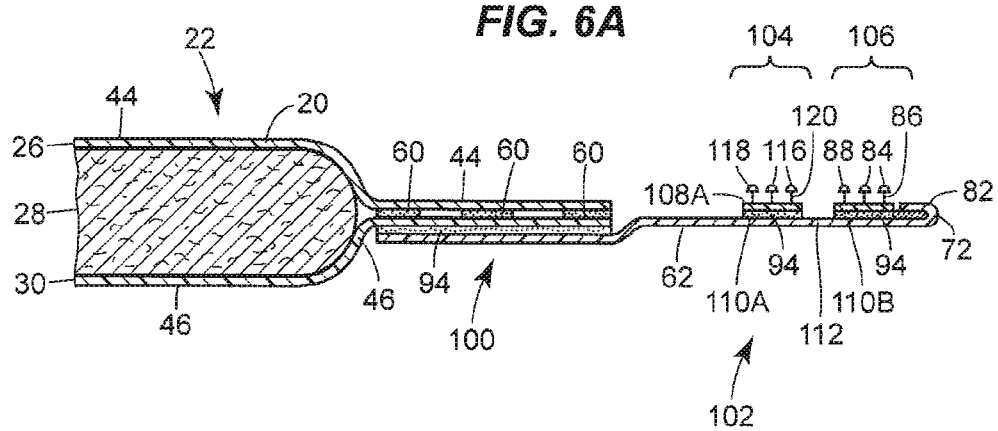
FIG. 6A is a cross-sectional view of a corner of the diaper illustrating an alternative embodiment of the fastener in an "open" position.
Figure 6B:
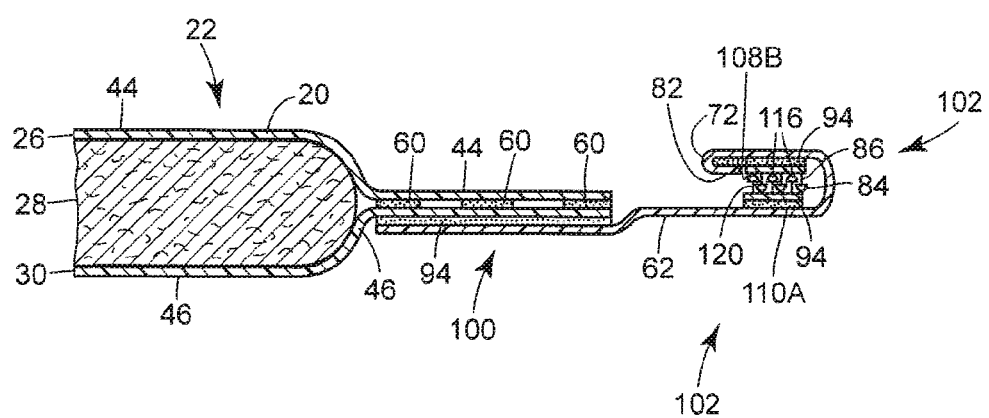
FIG. 6B is a cross-sectional view of the fastener of FIG. 6A in a "closed" position.
Figure 6C:
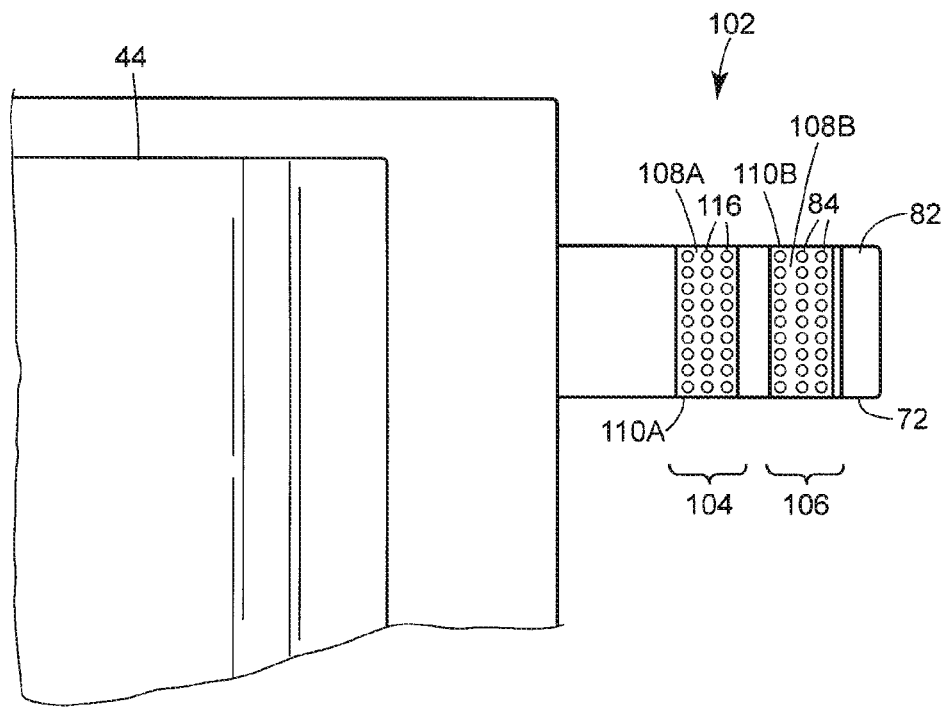
FIG. 6C is a top plan view of the fastener of FIG. 6A.

Another alternative embodiment of a suitable fastener is shown in FIGS. 6A through 6C. The proximate fastening member 104 of the fastener 62 shown in FIGS. 6A through 6C includes a plurality of engaging elements 116 outwardly extending from the proximate fastening surface 108A. As shown, each engaging element 116 includes a stem 118 supported at one end by the proximate fastening surface 108A and a head 120 disposed at the stem 118 end opposite the proximate fastening surface 108A.

FIG. 6B is a cross-sectional view of the fastener 62 of FIG. 6A shown in a "closed" position, for example, prior to the article's use by the diaper wearer. As shown in FIG. 6B, the fastening surfaces 108A and 108B and, more specifically, the engaging elements 116 and 84 of the respective surfaces 108A and 108B, are releasably fastenable to each other. When ready for use, the fastening surfaces (108A and 108B) may be disengaged from each other by the user. When these surfaces are disengaged from one another and laid in the "open" position (as shown in FIGS. 6A and 6C), the fastener 62 and, more specifically, the engaging elements 84 of the distal fastening surface 108B and the engaging elements 116 of the proximate fastening surface 108A, can engage the fastening surface 92 of the landing member 64 so as to provide a suitable side closure. In one embodiment, the proximate and distal fastening surfaces are laterally separated from each other on the connective portion by a distance of about 2 millimeters (mm) to about 8 mm.

Consistent with the embodiments illustrated in FIGS. 4A through 5C, the embodiment shown in FIGS. 6A through 6C provides a temporary bond having a peel strength and shear strength sufficient to maintain the fastener in a closed position during the article's manufacturing process, but weak enough to permit the article's user to readily open the fastener when the article is ready for use. In one embodiment, the engaged fastening elements of the proximate and distal fastening surfaces are capable of providing a bond having strength sufficient to maintain the fastener in a closed position during the article's manufacturing process, which bond approaches zero strength when the article's user removes the article from its packaging.

As discussed herein, fastener embodiments maintained in a closed position (as generally illustrated in FIGS. 2B, 3B, 4B, 5B, and 6B) will be subjected to peel forces in a variety of different contexts. Peel forces may be generated as the article is being assembled in a high-speed manufacturing process, for example. Furthermore, peel forces may be generated prior to the article's use (i.e., prior to the article being fit to the article's wearer) when, for example, the article is being packaged. Still further, peel forces may be generated by the article's user (e.g., a parent) when, for example, the user is preparing to fit the article to the wearer. User generated peel forces are expected to be much higher than the peel forces generated prior to the article's use by, for example, the article's manufacturing or packaging processes. In its closed position, the fastener embodiments are designed to have a resistance to peel forces (peel resistance) with respect to only the movements encountered during periods prior to the article's use. It should, therefore, be understood that the peel resistance should only be great enough to prevent the fastener, in its closed position, from opening prior to the article's use.

It has generally been found that these fasteners should be designed so as to resist peel forces of at least about 1 Newton (N), and less than about 5 N. In one embodiment, the peel forces of the fastener in a closed position should be about 1 N to less than about 5 N. In another embodiment, the peel forces should be at least about 2 N to less than about 4 N. Bond strength (or peel force) values can be measured according to a partially modified ASTM D 1876-95 (1995) (Standard Test Method for Peel Resistance also known as T-Peel Test) standard method, which is described in detail in Corzani U.S. Pat. No. 5,969,025

In use, and as described herein, the article 20 shown in FIG. 1 may be applied to the wearer by positioning the first end region 48 under the wearer's back and drawing the remainder of the article 20 between the legs of the wearer so that the second end region 50 is positioned across the front of the wearer. The connective portion of the fastener 62 is then secured to the outside surface 46 of the second end region 50 so that the landing member 64, which is disposed on the outside surface 46 of the second end region 50, will engage fastening members on the fastener 62 to form a side closure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fastener for a disposable absorbent article, the fastener being free of a release tape and comprising:
   (a) a fixed portion attachable to the article;
   (b) a connective portion joined to and contiguous with the fixed portion, the connective portion comprising
      (i) a distal edge,
      (ii) a fastening member having dissimilar proximate and distal fastening surfaces and a bonding surface opposite to the fastening surfaces, wherein at least one of the fastening surfaces is fastened to a layer of shedable nonwoven fabric on the article, and
      (iii) a backing member attached to the bonding surface of the fastening member; and,
   (c) a folding line disposed between the fixed and connective portions.

2. The fastener of claim 1, wherein the connective portion is foldable along the folding line to permit the at least one of the fastening surfaces to fasten to the layer of shedable nonwoven fabric.

3. The fastener of claim 1, wherein the proximate fastening surface is fastenable to the layer of shedable nonwoven fabric.

4. The fastener of claim 3, wherein the proximate fastening surface is an adhesive.

5. The fastener of claim 4, further comprising a plurality of engaging elements outwardly extending from the distal fastening surface.

6. The fastener of claim 5, wherein each engaging element comprises a stem supported at one end by the distal fastening surface and a head disposed at the stem end opposite the distal fastening surface.

7. The fastener of claim 5, wherein the distal fastening surface is releasably fastenable to a landing member on the article.

8. The fastener of claim 1, wherein the distal fastening surface is fastenable to the layer of shedable nonwoven fabric.

9. A disposable absorbent article comprising:
   (a) a body portion having an inside surface, an outside surface opposite of the inside surface, longitudinal edges, end edges, a first end region, and a second end region opposite of the first end region, the body portion comprising a liquid pervious topsheet, a liquid impervious backsheet joined to the topsheet, and an absorbent core disposed between the topsheet and the backsheet; and,
   (b) a fastener free of a release tape, the fastener comprising a fixed portion attached to the first end region of the body portion, and a connective portion joined to and contiguous with the fixed portion, a folding line disposed between the fixed and connective portions, wherein the connective portion comprises:
      (i) a distal edge,
      (ii) a fastening member having dissimilar proximate and distal fastening surfaces and a bonding surface opposite to the fastening surfaces, wherein at least one of the fastening surfaces is fastened to a layer of shedable nonwoven fabric on the inside surface of the body portion adjacent the fastener, and
      (iii) a backing member attached to the bonding surface of the fastening member.

10. The disposable absorbent article of claim 9, wherein the connective portion is foldable along the folding line to permit the at least one of the fastening surfaces to fasten to the layer of shedable nonwoven fabric.

11. The disposable absorbent article of claim 9, wherein the proximate fastening surface is fastenable to the layer of shedable nonwoven fabric.

12. The disposable absorbent article of claim 11, wherein the proximate fastening surface is an adhesive.

13. The disposable absorbent article of claim 12, further comprising a plurality of engaging elements outwardly extending from the distal fastening surface.

14. The disposable absorbent article of claim 13, wherein each engaging element comprises a stem supported at one end by the distal fastening surface and a head disposed at the stem end opposite the distal fastening surface.

15. The disposable absorbent article of claim 13, wherein the distal fastening surface is releasably fastenable to a landing member on the article.

16. The disposable absorbent article of claim 9, wherein the distal fastening surface is fastenable to the layer of shedable nonwoven fabric.

* * * * *